United States Patent [19]

Theeuwes

[11] 4,203,441
[45] May 20, 1980

[54] OSMOTICALLY TRIGGERED DEVICE WITH GAS GENERATING MEANS

[75] Inventor: Felix Theeuwes, Los Altos, Calif.
[73] Assignee: Alza Corporation, Palo Alto, Calif.
[21] Appl. No.: 970,537
[22] Filed: Dec. 18, 1978
[51] Int. Cl.² ............................................. A61M 31/00
[52] U.S. Cl. .............................. 128/260; 222/386.5; 428/327
[58] Field of Search ............... 128/260, 261, 268, 172, 128/203, 204, 219, 225; 222/386.5, 389, 399; 428/159, 206, 221, 327, 480, 481

[56] References Cited

U.S. PATENT DOCUMENTS

| | | | |
|---|---|---|---|
| 3,023,750 | 3/1962 | Baron | 222/386.5 |
| 3,114,371 | 12/1963 | Montague | 128/271 |
| 3,444,290 | 5/1969 | Wai | 424/44 |
| 3,592,672 | 7/1971 | Rowley et al. | 210/500 M |
| 3,797,492 | 3/1974 | Place | 128/260 |
| 3,840,009 | 10/1974 | Michaels et al. | 128/260 |
| 3,916,899 | 11/1975 | Theeuwes | 128/260 |
| 4,036,228 | 7/1977 | Theeuwes | 128/260 |
| 4,111,201 | 9/1978 | Theeuwes | 128/260 |
| 4,111,203 | 9/1978 | Theeuwes | 128/260 |

Primary Examiner—Robert W. Michell
Assistant Examiner—C. F. Rosenbaum
Attorney, Agent, or Firm—Paul L. Sabatine; Thomas E. Ciotti; Edward L. Mandell

[57] ABSTRACT

A device is disclosed for supplying and delivering an useful agent. The device comprises (1) a housing defining an internal space, (2) a flexible container in the housing and having a passageway for connecting the container with the exterior of the device, (3) a useful agent in the container, and (4) a gas generating means located between the housing and the container. In operation, when the device is in a fluid environment, fluid is admitted into the device and contacts the means, causing it to produce a gas that exerts pressure against the container. The pressure urges the container to decrease its dimensions and correspondingly deliver agent through the passageway from the device. Also, article of manufactures are enclosed, which articles consists of a gas generating means between two different polymeric films, and a gas generating means housed in a polymeric matrix.

15 Claims, 7 Drawing Figures

OSMOTICALLY TRIGGERED DEVICE WITH GAS GENERATING MEANS

FIELD OF THE INVENTION

This invention pertains to both a new and useful self-contained, self-powered unit device for supplying and delivering a beneficial agent. More particularly, the invention relates to an integral device that delivers an agent in response to a solid gas generating means producing a gas that is applied as a gaseous force against a container. The force causes the container to collapse and decrease its internal volume, thereby delivering agent from the device to the environment of use. The invention also concerns a three-layered composition of matter consisting essentially of a gas generating means positioned between two different polymeric films, and it concerns a gas generating couple within a polymeric matrix.

THE PRIOR ART

In recent times, much research effort has been devoted to developing new and useful devices for delivering useful agents to a preselected environment of use. For example, U.S. Pat. No. 3,760,984, issued to Theeuwes discloses a device comprising an inner collapsible container carrying on its outer surface a layer of an osmotic solute and a distant layer of a polymer permeable to fluid and impermeable to the solute. The device has an inventive means for filling the container. In U.S. Pat. No. 3,971,376, issued to Wichterle, a device is disclosed comprising a capsule having a unitary wall formed of a substantially noncollapsible elastic material that maintains a constant volume and is exposed to the environment of use. A textile fabric is imbedded in the elastic material to strengthen the material and act as a reinforcement. In U.S. Pat. No. 3,987,760, issued to Eckenhoff, et al., there is disclosed a fluid flow moderator comprising a conduit that fits into an osmotic device to provide an outlet for dispensing fluid from the device. In U.S. Pat. No. 3,995,631, issued to Higuchi, et al., there is disclosed a bag formed of a flexible material encapsulated with an osmotically effective solute surrounded by a wall having in at least a part controlled permeability to an external fluid. The above-described osmotic devices are useful for delivering many agents, and they each represent a valuable contribution to the agent delivery art. The present invention is a further advancement in the delivery art by making available a novel device that provides a new delivery profile for in vivo and vitro delivery of a useful agent.

OBJECT OF THE INVENTION

It is an immediate object of this invention to provide both a novel and useful agent formulation delivery device that is self-contained and self-powered, and also represents an improvement in the delivery art.

Another object of the invention is to provide a delivery device that is simple in construction and dimensioned for use in a multiplicity of environments, and which device can produce the practical benefits of delivering beneficial agents at high flow rates in a limited time period.

Yet another object of the invention is to provide a three-layered article of manufacture useful for fabricating an agent delivery device.

Yet another object of the invention is to provide a device that has a high volume delivery rate in a short unit of time, and can be used to deliver a drug to animals including humans.

Still another object of the invention is to provide a delivery device that has a quick onset of delivery action, and can be used to deliver from low to high concentrations of active agent from the device, and which concentrations of agent will not be leaked from the device, nor have their potency decreased during delivery to the environment of use.

Still another object of the present invention is to provide a delivery device that is easy to manufacture, and will deliver thixotropic formulations at a controlled and continuous rate in a short period of time.

Yet another object of the invention is to provide a gas generating couple dispersed in a polymer matrix that can be used for generating gas.

Other objects, features and advantages of this invention will become more apparent from the following detailed description when taken in conjunction with the accompanying specification, the drawings, and the claims.

SUMMARY OF THE INVENTION

This invention concerns a device for delivering a beneficial agent to an environment of use. The device comprises a gas generating member surrounding a flexible container filled with agent and positioned in a housing member. In operation, the device release agent under pressure in response to fluid entering the device by imbibition causing the gas generating member to produce gas and internally pressurize the device. The internal, gaseous pressure is exerted against the container, thereby diminishing its internal volume, which combination of imbibition, gas-pressure and diminishing volume actions urges agent from the device. The invention also concerns a three-layered laminate and a gas generating couple in a polymer matrix that are useful for making the delivery devices.

BRIEF DESCRIPTION OF THE DRAWINGS

In the drawings, which are not drawn to scale, but are set forth to illustrate various embodiments of the invention, the figures are as follows.

In the drawings and specification, like parts in related Figures are identified by like members. The terms appearing earlier in the specification and in the description of the drawings, as well as in embodiments thereof, are further described elsewhere in this disclosure.

DETAILED DESCRIPTION OF THE DRAWINGS

Figure 1A:
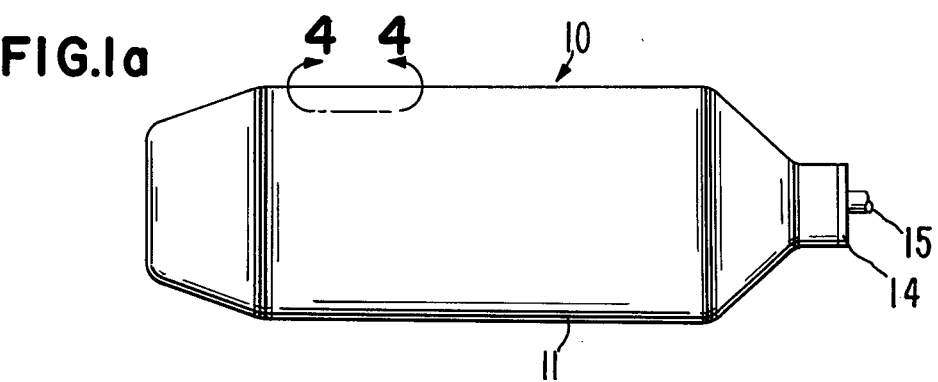
FIG. 1a is a front, elevational view illustrating a delivery device made according to the mode and manner of the invention.
Figure 1B:
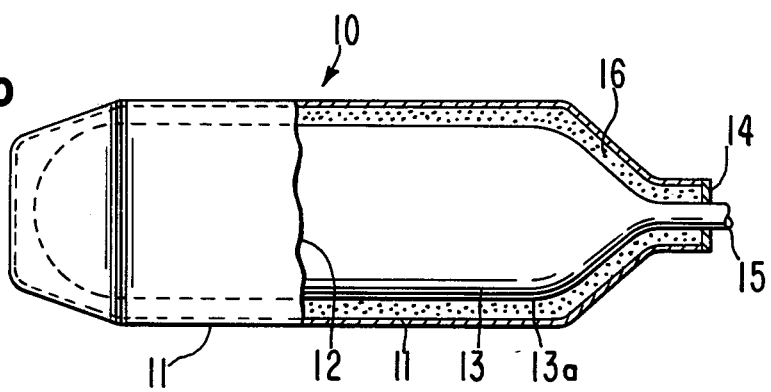
FIG. 1b is an opened-section view of the device of FIG. 1a illustrating the members forming the integral device.
Figure 2A:
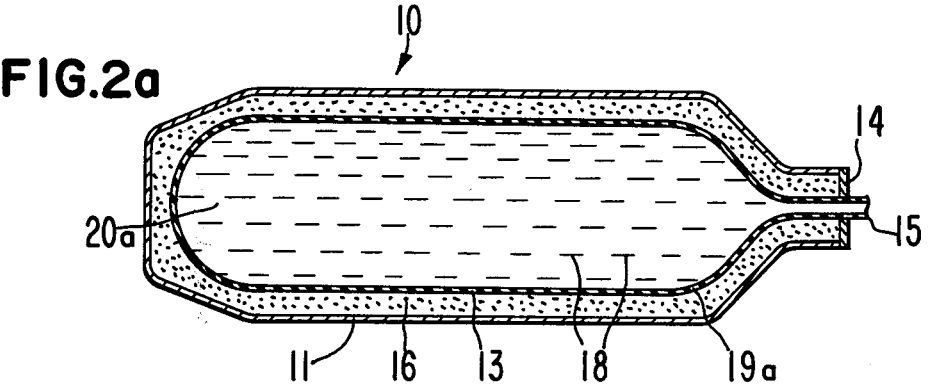
FIGS. 2a and 2b are full, opened views of the device of FIG. 1, depicting the structure and the operation of the device.
Figure 2B:
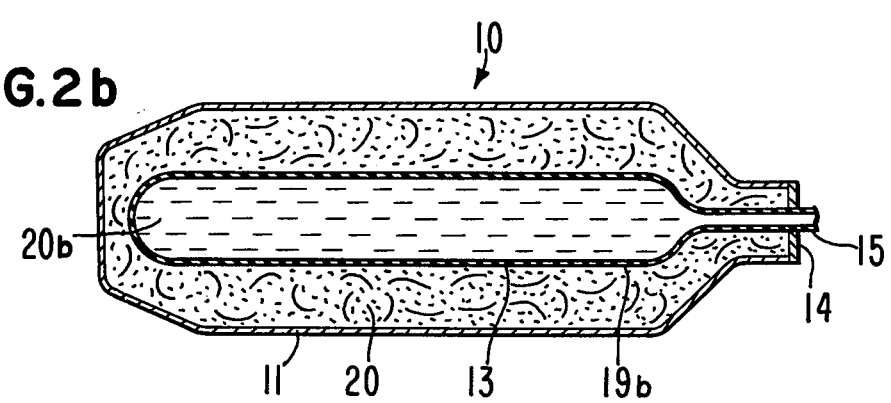

Turning now to the drawings in detail, which are an example of a new and useful device for delivering an agent, and which example is not to be construed as limiting, one device is indicated in FIG. 1a and FIG. 1b by numeral 10. In FIG. 1a, device 10 consists essentially of a housing 11 designed, shaped, sized and adapted for placement and retention in the environment of use. Housing 11, in a presently prefered embodiment, is seen in FIG. 1b at opened section 12, which housing 11 is, in a presently preferred embodiment, made of a substantially rigid wall 11 forming material. Housing 11 in this invention is wall 11 forming the exterior member of device 10. Housing 1 surrounds and defines an internal space for holding a flexible container 13. Housing 11 has at least one opening 14, or it can have more than one opening through which container 13 communicates through passageway 15 with the exterior of device 10. Passageway 15 is used for admitting an agent formulation, not seen in FIG. 1b, into container 13, and for delivering an agent formulation from container 13 of device 10. Container 13 is formed of a flexible material that can move from a rested state to a diminished state, for example, container 13 can collapse in response to pressure applied against its exterior surface 13a. The movement of container 13 from a resting state to a collapsed state produces an internal volume change, as seen in FIGS. 2a and 2b, that propels agent from device 10. A gas generating means 16, also is seen in FIG. 1b, is positioned between wall 11 and container 13.

Referring to FIGS. 2a and 2b, dispensing device 10 is seen in full opened-section comprising wall 11 formed of a substantially shaped retaining rigid material having positioned therein gas generating member 16 and flexible container 13. Container 13 is partially or completely surrounded by member 16. Member 16 is positioned adjacent to and/or carried on the interior surface of wall 11 and the exterior surface 13a of container 13. Wall 11 is made of a semipermeable material substantially impermeable to the passage of gas producing chemical compounds, and has a low permeability to the passage of an external fluid and an internal produced gas. Container 13 is formed of an elastomeric, or other low modulus material, and it, 13, has a passageway 15 for dispensing agent formulation 18 from device 10 to the environment of use. Passageway 18, in one embodiment, is formed by the wall of container 13, terminating in passageway 15, which is projected through opening 14 of housing 11. Gas generating means 16 consists essentially of a dry compound, or an anhydrous mixture of compounds, or a gas generating couple in a matrix that when intimately contacted by fluid that enters device 10 generates a gas-powered device 10.

In operation, member 16 imbibes external fluid into housing 11 to continuously wet and dissolve gas generating means 16, causing it to react and produce a large volume of gas 20, which gas 20 is illustrated as curved-lines 20. Gas 20, in FIGS. 2a to 2b, expands and than exerts a gaseous force against container 13, filling the area between wall 11 and container 13. This action correspondingly causes container 13 to collapse from position 19a to 19b. The collapse of container 13 decreases the internal volume of container 13 from 20a to 20b, thereby expelling agent formulation 18 through passageway 15 to the environment of use. The rate of fluid imbition, $R_I$, of member 16 across wall 11 coupled with the rate of gas generated, $R_G$, and the rate of volume change, $R_V$, act in concert to control the rate of release, $R_R$, of agent 18 from device 10. The size of passageway 15 can in an optional embodiment be given predetermined dimensions as an additional aid for governing the rate of release of formulation 18 from device 10.

Figure 3:
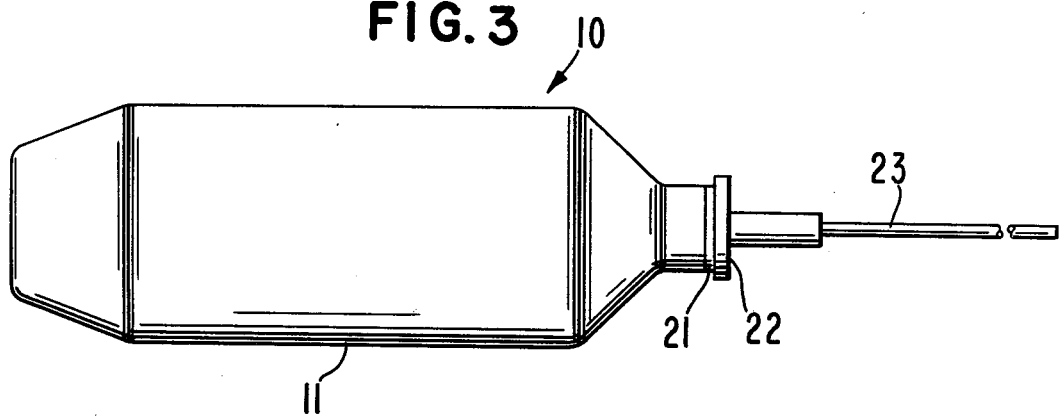
FIG. 3 illustrates the device of FIG. 1 adapted for receiving a tube for dispensing agent to an agent receptive site distant from the device.

FIG. 3 is similar to FIG. 1a with the added features that device 10 of FIG. 3 comprising housing 11 embodies an adaptor 22 that sealingly engages housing 11 at its terminal end 21, which adaptor is a means for connecting a conduit or tube 23 to device 10. Adaptor 10 sealingly engages device 10 for preventing any possible loss of gas and fluid from device 10. This latter design parallels the design of FIG. 1a wherein the passageway from the inside to the outside of the device is manufactured or sealed to prevent the passage of gas and fluids from device 10.

Figure 4:
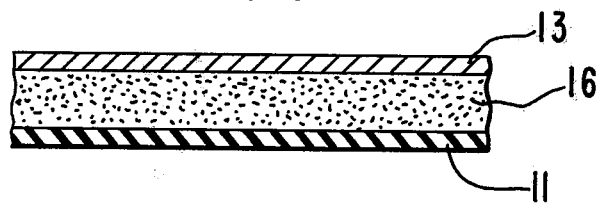
FIG. 4 illustrates a three-layered laminate useful for generating gas pressure for powering the delivery device of FIG. 1; and, FIG. 5 illustrates an apparatus for measuring the permeability and rate of gas diffusion through polymeric walls forming the device of FIG. 1.

FIG. 4 illustrates a view taken through 4—4 of FIG. 1a. FIG. 4 shows a superposed laminar arrangement comprising three-layers. The layers are identified as wall or layer 11 formed of a semipermeable polymer, gas generating means or layer 16 that yields the gas for powering the device, and the wall of the container or layer 13 which is formed of a flexible material that collapses in operation to produce the intended results. Also, layer 16 in another embodiment can consists of a gas generating couple in a polymer matrix. The three-layered article can be made as an integral part of device 10, or it can be made independently as an article of manufacture and subsequently fabricated into a device. The wall layer, the gas generating means layer and the flexible layers are referred to as first, second and third layers for identifying their position in the article of manufacture.

Figure 5:
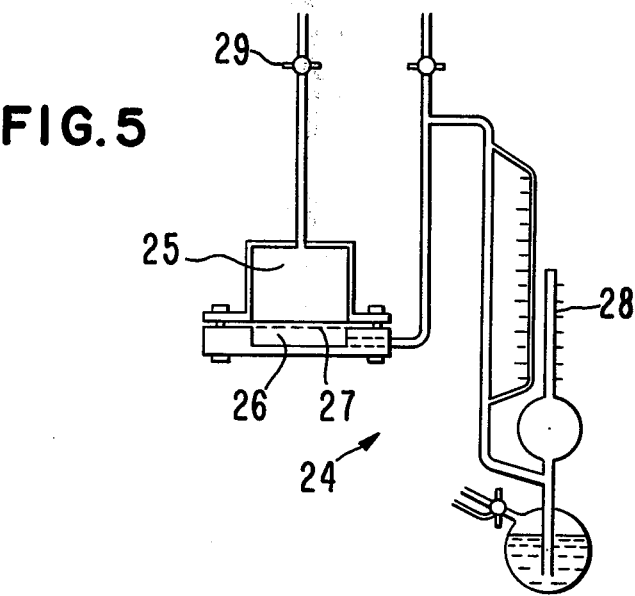

FIG. 5 shows an apparatus 24 useful for selecting material for making device 10. Apparatus 24 can be used for measuring permeability and subsequently ascertaining the rate of diffusion of materials having a lower permeability and diffusivity than the rate of gas generated, which indicates their use for the making of a gas-powered device. Apparatus 24 comprises a gas cell made of two parts of steel, part 25 and part 26. Parts 25 and 26 are gas chambers separated from each other by membrane 27. To prevent membrane 27 from sagging it can optionally be supported on a fine gauge net. In use, gas such as carbon dioxide, is introduced through valve 29 into chamber 25, which chamber is connected to pressure gauge 28. Pressure gauge 28 can be a standard McLeod pressure gauge with a range up to 2.5 mm Hg pressure and recording with an accuracy of 0.005 mm Hg pressure. The apparatus can be used according to the procedure described in *The Permeability of Different Rubbers to Gases and Its Relation to Diffusivity and Solubility*, by van Amerongen, in *J. of App. Phy.*, Vol. 17, pages 972 to 985, 1946. Thus, by noting the increase in pressure in the apparatus due to the permeability of the membrane, the permeability can be calculated and the rate of diffusion ascertained. Procedures that can be used for this purpose, and a like apparatus, are described by Barrer in *Trans. Faraday Soc.*, Vol. 35, 628, 1939 and by Daynes in *Proc. Roy. Soc.*, Vol. A97, 286, 1920.

While FIGS. 1 through 4 are illustrative of various devices that can be made according to the invention, it is to be understood these devices are not to be construed as limiting, as they can take a wide variety of shapes, sizes and forms for delivering an agent including a drug to many and varied different environments of use. For example, device 10 can be manufactured for dispensing drug to animals, which term includes warm-blooded mammals, humans, household, farm, sport, and zoo animals. The devices can also be used for dispensing drugs to avians, pisces and reptiles. Device 10 can be structured, sized, shaped and adapted for delivering drug to body cavities and body openings, and for use in oral, implant, intramuscular, intrauterine, vaginal, cervical, rectal, nasal, ear and dermal applications. Device 10 also can be used as an artificial gland, and for the arterial and venous administration drug. The device can be used in homes, hospitals, clinics, ships, laboratories, factories, and the like.

DETAILED DESCRIPTION OF THE INVENTION

Device 10, as used for the purpose of this invention consists of housing 11 made of a polymer possessing rigid properties. The polymer also is substantially impermeable to the passage of solids and exhibits limited permeability to the passage of fluid and gas. These combination of properties permit gaseous pressure to be exerted against housing 11 without any major change in its shape or dimensions, and restricts the possible loss of gas from the device, thereby assuring that gas-pressure generated in device 10 is exerted against container 13. Representative materials suitable for forming housing 11 include semipermeable polymers such as a member selected from the group consisting of cellulose acylate, cellulose diacylate, cellulose triacylate, cellulose acetate, cellulose diacetate, cellulose triacetate, cellulose esters and cellulose ethers. Generally, the thickness of the housing will vary depending on the device and its use, and it will usually have a thickness of from 0.25 mm to 15 mm, or more.

Representative materials suitable for manufacturing container 13 are materials that can be designed and dimensioned into a shaped, changable volume container, that exhibits low permeability to the passage of gas generated in the device, collapse in response to applied gaseous pressure, thereby dispensing agent, and can exist in laminar arrangement with the housing and the means for generating a gas. Typical flexible, elastomeric polymers include natural rubber, often identified by the synonyms poly(2-methyl-1,3-butadiene) and cis-1,4-polyisoprene, gutta percha or trans-polyisoprene, cyclised rubber, synthetic isoprene rubber, butadiene rubber, styrene-butadiene rubber, nitrile rubber, chloroprene rubber, ethylene-propylene rubber, butyl rubber, methyl rubber or poly(piperylene) rubber, and the like. The rubbers are commercially available as Buna S or butadiene-styrene copolymer, poly(2,3-dimethyl-1,3-butadiene), Perbunan or butadiene-acrylonitrile copolymer, Neoprene G or poly(2-chloro-1,3-butadiene), Opanol B-200 or polyisobutylene, Mipolam MP or vinyl chloride-acrylonitrile copolymer, Thiokol B or condensation product of sodium tetrasulfide and dichlorodiethyl ether rubber. The rubbers are disclosed in *Handbook of Common Polymers*, by Scott and Roff, Sections 29 through 40, 1971, published by the Chemical Rubber Company, Cleveland, Ohio; *Encyclopedia of Polymer Science and Technology*, pages 406 to 409, 678 to 704, and 705 to 716, 1966, published by McGraw-Hill, Inc., New York; and in *Handbook of Plasters and Elastomers*, by Harper, Chapters 2 and 3, 1975, published by McGraw-Hill Book Company, San Francisco, Calif. Container 13, formed of the representative materials, can have its wall of varying thickness, usually about 0.25 mm to 15 mm, or more, depending on the container and its uses. Container 13 can be manufactured with one or more passageways for dispensing agent, or it can be made to form a passageway when the device is in the environment of use. In this latter embodiment, one end of container 13 is closed with a water-soluble plug, or an erodible material, such as polyvinyl alcohol, or the like, that erodes in the environment of use to form a small-diameter orifice. In another embodiment, a preformed orifice having a cross-section of 1 to 10 mils can be temporarily closed with a plug, which plug is ejected when the chamber starts to collapse and pump agent during use, thereby forming the orifice in situ.

The gas generating means, 16, suitable for the purpose of the present invention comprises a preferably solid acidic material, and a preferably solid basic material that dissolve and react in the presence of aqueous fluid that enters device 10 to produce a gas. The latter gas exerts gaseous pressure against container 13 causing it to decrease in size and dispense agent 18 from device 10. The gas generating means in device 10 can be in powder, crystalline, granular or layered form. The acids that can be used include anhydrous pharmaceutically acceptable organic acids, the acid salts, and mixtures thereof such as malic, fumaric, tartaric, itaconic, maleic, citric, adipic, succinic, glycine, and mesaconic, the corresponding anhydrides such as itaconic anhydride and citriconic anhydride. Also, inorganic acids can be used such as sulfamic and phosphoric, and the acids disclosed in U.S. Pat. No. 3,325,357. The acid salts of commonly used acids can be used such as monosodium citrate, disodium citrate, potassium acid tartrate and potassium bitartrate; the monoalkali metal phosphates such as monosodium phosphate and monopotassium phosphate and other salts such as monoammonium phosphate and ammonium biphosphate. In some applications, the gas generating couple may be a single compound like calcium carbide that reacts with water and produces gas.

In another embodiment gas generating couple 16 is present homogenously or heterogenously dispersed in a matrix. The matrix is a polymer permeable to the passage of fluid, particularly water and permeable to the passage of gas generated in device 10. The rate of gas generated in this embodiment is governed by the rate of fluid passage through the polymer coupled with the rate of fluid passage through semipermeable wall 11 of device 10. The gas generated in this embodiment is applied against container 13. Typical polymer that can be used for containing gas generator 16 include polyolefins and vinyl polymers; poly(hydroxyalkyl methacrylate); poly(acrylamide); gitatin; carbohydrates; poly(methacrylamide); poly(N-vinyl-2-pyrrolidone); dextran; anionic and cationic hydrogels; poly(electrolyte) complexes; lightly cross-linked poly(vinyl alcohol); poly(vinyl alcohol); poly(glyceryl methacrylate); poly(hydroxypropyl methacrylate); poly(sulphide); poly(vinyl acetate); poly(sulphoxide); poly(sulphone); poly(styrene); copolymeric(divinylbenzene-styrene); poly(dialkylaminoethyl styrene); cation and anion exchange resins; collodin; sulfonated copolymers of styrene and divinylbenzene; copolymers of methacrylic and divinylbenzene; poly(urethane); cellulose esters; cellulose ethers; polymers that undergo a decrease in the glass transition temperature in the presence of water; plasticized polymers of the above; and the like. In a presently preferred range, for slow gas generation, there is present from 1 to 30% of gas generating couple per 100 weight percent of combined couple and polymer; and for a faster, higher rate of gas production from 30 to 95% of gas generating couple for 100 weight percent combined couple and polymer. In addition to preselecting the rate of water permeability of the matrix, particle size, osmotic activity and percent loading can be selected as means for governing the rate of gas production.

The basic compounds include the pharmaceutically acceptable carbonate-containing materials which react with the acidic materials with the release of carbon dioxide when contacted with water. These materials include metal carbonates and bicarbonate salts, such as alkali metal carbonates and bicarbonates, alkaline earth bicarbonates and carbonates, and mixtures thereof. Exemplary materials include ammonium carbonate, ammonium bicarbonate, ammonium sesquicarbonate, and magnesium carbonate, and more particularly the alkali metals such as sodium carbonate, sodium bicarbonate, sodium sesquicarbonate, potassium carbonate, potassium bicarbonate, and mixtures hereof. The combination of certain of these acids and bases results in a more rigid gas production when contacted by water than do other of the above-listed groups. In particular, either citric acid or a mixture of citric acid and tartaric acid and sodium bicarbonate give a rapid gaseous reaction that is useful for quickly increasing the gas volume for its pressure against container 13. This selection leads to a quick dispersing of the active agent. The gas generating couple is preferably formed of substantially stoichiometrically balanced parts to produce a combination that generates carbon dioxide. Also, dry lubricating agents, such as gelatin, acacia, lactose and the like may be used to layer or coat the gas generating means onto the exterior of container 13.

The term active agent as used herein means any compound that can be delivered to produce a useful or beneficial result. These include agents that can be delivered at high flow rates, in a short time period, when a small amount of moisture in a low-moisture environment passes into the device and triggers the gas generating means to produce gas. In this instance the device has a high volume delivery rate per unit time. The term agent includes algicide, antioxidant, biocide, germicide, fungicide, pesticide, rodenticide, insecticide, plant growth promoter, plant growth inhibitor, preserving agents, surfactant, disinfectant, catalyst, sterilization agent, chemical reactant, fermentation agent, cosmetic, food, nutrient, food supplement, drug, vitamin, sex sterilant, fertility inhibitor, fertility promoter, air purifier, microorganism attenuators, and other compounds that benefit the surroundings, the environment, and the habitat.

Exemplary drugs that can be administered according to the spirit of the invention include locally and systemically acting drugs. These drugs include a member selected from the group consisting of physiologic and pharmacologic acting drugs, such as gastrointestinal administrable drugs, central nervous and autonomic nervous system acting drugs, hypnotic, sedative, psychic energizer, tranquilizer, anticonvulsant, antiparkinson, antiallergenic, muscle relaxant, analgesic, antipyretic, anti-inflammatory, anesthetic, antispamodic, antimicrobial, antivirial, antiulcer, hormonal, sympathomimetic, diuretic, hypoglycemic, vitamin, contraceptive, and opthalmic drugs. These benefical drugs and their dose amounts for humans are known in *Drill's Pharmacology in Medicine*, edited by DiPalma, J. R., 1965, published by McGraw-Hill Book Company, New York; in *Pharmacological Basis of Therapeutics*, by Goodman and Gilman, 4th Edition, 1970, published by the McMillian Company, London; in *The Drug, The Nurse, The Patient*, edited by Falconer, Ezell, Patterson and Gustafson, 1974, published by W. B. Saunders Company, Philadephia; and in U.S. Pat. No. 3,977,404, which patent is assigned to the Alza Corporation of Palo Alto, Calif., the assignee of this patent application.

The drug in the container can be mixed with a pharmaceutically acceptable carrier, such as a liquid including water, saline, vegetable oils, cottonseed oil, sesame oil, ethyl oleate, isopropyl myristate, propylene glycol, 0.01% gelatin in oil, and the like. The drug can be present in solution, in semi-solid, or paste formulation, in a thixotropic state and the like, which permits controlled dispensing of drug from the device. Pharmaceutically acceptable carriers and the like are known to the art in *Remington's Pharmaceutical Sciences*, 4th Edition, pages 1461 to 1972, 1970, published by the Mack Publishing Company, Easton, Pa.

Representative examples of drugs that can be delivered from a device designed and adapted for oral administration comprise, (a) a housing manufactured from semipermeable cellulose acetate having an acetyl content of 38.3% and an opening for a passageway, and having housed therein, (b) a container shaped and sized like a triple zero capsule with a passageway for releasing drug and formed of flexible, natural rubber, which container is surrounded by (c) a coating interposed between the housing and the container, the coating a gas generating means. The means is coated from a composition consisting essentially of 56.7% potassium hydrogen carbonate, 40.2% citric acid and 3% polyvinyl pyrrolidone in anhydrous ethanol and evaporated prior to forming the housing by air coating, and a drug formulation in the container, such as (d) the antibiotic tetracycline hydrochloride in pharmaceutically acceptable polyethylene glycol 200, or (e) micronized procaine penicillin in silicone oil with a small amount of aluminum monostearate, which embodiments are dispensed at a useful rate from the devices, when the devices are in a fluid environment of use.

Another improved dispensing device embracing the structural members acting together is manufactured as follows: first, a cylindrical shaped container 2.33 cm long, 3.81 mm inside diameter and 4.67 mm outside diameter, is injection molded as 180° C., at 77-84 kg/cm$^2$, from the elastomeric copolymer styrene-butadiene. Next, a mandrel is inserted into the container, the assembly placed into a two-piece cavity mold, and the mold filled with light filling pressure with a mixture made of 25 mg of citric acid, 45 mg of sodium bicarbonate and 0.125 mg of ethylene maleic anhydride copolymer. Next, the mold is removed, and the mandrel-supported gas generating coated container dipped into a solution of cellulose acetate in acetone, 15 wt% with an acetyl content of 39.8%. The mandrel-supported coated container is dipped into the solution 20 times for 1 minute per dip, with an intervening 15 minute drying period. Following the dipping, the device is dried at 60° C. for 15 days. This procedure applies a 0.65 mm lamina of the semipermeable polymer on the gas generating lamina. The device is filled prior to use through the passageway.

Another improved gas-generating, gas-powered dispensing device is manufactured by following the procedures described above. The device is made by surrounding an elastomeric container with a matrix consisting essentially of a gas generating couple of 30% succinic acid and potassium carbonate dispersed in a poly(urethane) film, up to 100% by weight of combined polymer and couple. The semipermeable wall is applied by dipping into a solution consisting essentially of cellulose acetate having an acetyl content of 38.3% in 90:10 methylene chloride:acetone. The device is filled with drug through the passageway integral with the container.

Although the foregoing invention has been described in detail by way of a full disclosure, illustrations of presently preferred embodiments, and examples for the purpose of clarity of understanding it will be understood that certain changes and modifications may be practiced within the scope and spirit of the invention.

I claim:

1. A device for delivering a useful agent to an environment of use, comprising:
   (a) a useful agent;
   (b) a housing comprising a shape-retaining wall formed of a semipermeable polymer that defines an internal space and has an opening that connects the space with the exterior of the device;
   (c) a container in the housing, said container comprising a flexible wall surrounding a reservoir for storing the agent, and a passageway that passes through the opening for delivering the agent from the container to the exterior of the device; and,
   (d) means for generating a gas in the device interposed between the housing and the container, said means generating gas in response to fluid admitted into the device, which gas exerts pressure on the container causing it to decrease in volume and correspondingly delivers agent through the passageway from the device in a unit time.

2. The device for delivering a useful agent to an environment of use according to claim 1, wherein the container is formed of a member selected from the group consisting essentially of natural rubber, gutta percha rubber, cyclised rubber, isoprene rubber, butadiene rubber, styrene-butadiene copolymer rubber, nitrile rubber, chloroprene rubber, ethylene-propylene rubber, butyl rubber, poly(piperylene) rubber, poly(2,3-dimethyl-1,3-butadiene) rubber, butadiene-acrylonitrile rubber, poly(2-chloro-1,3-butadiene) rubber, poly(isobutylene) rubber, vinyl-chloride-acrylonitrile copolymer rubber, and the condensation product of sodium tetrasulfide and dichlorodiethyl ether rubber.

3. The device for delivering a useful agent to an environment of use according to claim 1, wherein the agent is a drug.

4. The device for delivering a useful agent according to claim 1 wherein the environment is a biological environment, and the agent is a drug selected from the group consisting of locally and systemically acting gastrointestional, nervous system, hypnotic, sedative, psychic energizer, tranquilizer, anticonvulsant, antiparkinson, muscle relaxant, analgesic, antipyretic, antiinflammatory, anesthetic, antispasmodic, antimicrobial, antiviral, antiucler, hormonal, sympathomimetic, diuretic, hypoglycemic, and contraceptive drugs.

5. An article of manufacture useful for fabricating a gas-powered device for delivering a beneficial agent to an agent receptive environment, the article comprising a first layer of a polymer selected from the group consisting of cellulose ester, cellulose ether, cellulose acylate, cellulose diacylate and cellulose triacylate, the first layer positioned adjacent to a second layer which second layer comprises a means for generating a gas, and which second layer is in contacted arrangement with a third layer of a flexible, elastomeric polymer.

6. The article of manufacture useful for fabricating a gas-powered device for delivering a beneficial agent according to claim 5 wherein the means for generating a gas comprises an acidic component and a basic component which when brought into fluid reactive environment generate gas.

7. A gas-powered dispensing device comprising:
   (a) a container for storing a beneficial agent, said container changeble from a storing to a substantially emptied state;
   (b) a passageway for connecting the container with the exterior of the device for dispensing agent from the device;
   (c) means for generating gas on the exterior surface of the container, said means comprising an acidic component and a basic component that react in the presence of aqueous fluid admitted into the device and generate a gas;
   (d) a wall for maintaining the physical shape and dimensions of the device, and for admitting fluid into the device, the wall surrounding and enclosing the container and the gas generating means; and
   (e) wherein, when the device is in operation, in a fluid environment, fluid is admitted into the device causing the means to generate gas that is applied against the container, urging the container to undergo change to an empty state, thereby dispensing agent through the passageway from the device in unit time.

8. The gas-powered dispensing device for dispensing a beneficial agent according to claim 7 wherein the acidic component is a member selected from the group consisting essentially of malic, fumaric, tartaric, itaconic, malric, citric, adipic, succinic, mesaconic and glycine, and the basic component is a member selected from the group consisting essentially of sodium carbonate, potassium carbonate, magnesium carbonate, sodium bicarbonate, potassium bicarbonate, magnesium bicarbonate, and mixtures thereof.

9. The gas-powered dispensing device for dispensing a beneficial agent according to claim 7 wherein the device is sized, shaped and adapted for use in a fluid environment which environment is the gastrointestinal tract.

10. The gas-powered dispensing device for dispensing a beneficial agent according to claim 7 wherein the acidic component is a member selected from the group consisting of inorganic acids, organic acids, salts of acids and mixtures thereof, and the basic component is a carbonate containing component, selected from the group consisting of alkali metal carbonates, alkali metal bicarbonates, alkaline earth carbonates, alkaline earth bicarbonates, and mixtures thereof.

11. The device for delivering a useful agent to an environment of use according to claim 1, wherein the means for generating gas is calcium carbide.

12. An article of manufacture useful for generating a gas in a fluid environment comprising a gas generating couple consisting of an acidic component and a basic component dispersed in a polymer that is permeable to the passage of fluid, said polmer a member selected from the group consisting of polyolefins and vinyl polymers, poly(hydroxyalkyl methacrylate), poly(acrylamide), gelatin, poly(methacrylamide), poly(N-vinyl-2- pyrrolidone), dextran, carbohydrate, anionic and cationic hydrogels, poly(electrolyte) complexes, lightly cross-linked poly(vinyl alcohol), poly(vinyl alcohol), poly(glyceryl methacrylate), poly(hydroxypropyl methacrylate), poly(sulphide), poly(sulphoxide), poly(sulphone), poly(styrene), copolymeric(divinylbenzene and styrene), poly(dialkylaminoethyl styrene), cation and anion exchange resins, collodin, sulfonated copolymers of styrene and divinylbenzene, copolymers of methacrylic and divinylbenzene, poly(urethane), cellulose esters, and cellulose ethers, and wherein the article when in a fluid environment admits fluid into the polymer causing the couple to react and generate gas that is released from the polymer over time.

13. An article of manufacture useful for generating gas according to claim 12 wherein the polymer exhibits a decrease in the glass transition temperature in the presence of fluid.

14. An article of manufacture useful for generating gas according to claim 12 wherein the article consists essentially of from 1 to 30% of of gas generating couple up to 100% by weight of combined polymer and couple.

15. An article of manufacture useful for generating gas according to claim 12 wherein the article consists essentially of from 30 to 95% of gas generating couple up to 100% by weight of combined polymer and couple.

* * * * *